United States Patent [19]

Halkyard

[11] Patent Number: 4,915,701
[45] Date of Patent: Apr. 10, 1990

[54] PROTECTIVE DEVICE AND SYRINGE

[76] Inventor: Douglas R. Halkyard, 4300 Sandridge Rd., Morris, Ill. 60450

[21] Appl. No.: 312,794

[22] Filed: Feb. 21, 1989

[51] Int. Cl.$^4$ .............................................. A61M 5/00
[52] U.S. Cl. ..................................... 604/198; 604/232; 604/241
[58] Field of Search ............... 604/198, 192, 187, 232, 604/263, 240-243

[56] References Cited

U.S. PATENT DOCUMENTS

| | | | |
|---|---|---|---|
| 2,875,760 | 3/1959 | Haber | 604/242 |
| 4,740,205 | 4/1988 | Seltzer et al. | 604/241 X |
| 4,840,619 | 6/1989 | Hughes | 604/198 X |

Primary Examiner—John D. Yasko
Attorney, Agent, or Firm—Ernest Kettelson

[57] ABSTRACT

A protective device for a re-useable syringe comprising a tubular sheath mounted on the syringe barrel for reciprocal movement therein between an extended position wherein it covers the hypodermic needle connected to the syringe and a retracted position wherein the needle connecting end of the syringe barrel is exposed to enable connecting a new sterile hypodermic needle thereto. The tubular sheath has a plurality of longitudinal grooves to receive corresponding longitudinal ribs of the barrel therein to provide enhanced stability of the tubular sheath to hold it more securely in axial alignment with the syringe barrel when in the extended position to thereby prevent the wall of the tubular sheath from being moved out of axial alignment where it could come in contact with the needle which it encompasses. The tubular sheath has access openings near its rearward end which overlie the hub of the hypodermic needle when the sheath is in its extended position, thereby enabling the user to reach in and unscrew the hub of the needle assembly from the syringe barrel after the needle has been used. The disconnected needle can then be carried in the cavity of the tubular sheath while held in the horizontal position to a disposal container and dropped therein by tipping the syringe and tubular sheath downward. The used needle can then slide out the open end of the sheath into the disposal container.

18 Claims, 5 Drawing Sheets

PROTECTIVE DEVICE AND SYRINGE

BACKGROUND OF THE INVENTION

This invention relates to protective devices for syringes which protect the user from accidental puncture by the hypodermic needles attached to the syringe. In particular, this invention relates to protective devices for the permanent type of syringe which is repeatedly re-useable for a relatively long period of time before it has to be replaced or discarded.

A protective device for a re-useable syringe should itself be re-useable for the same length of time as the syringe, or re-useable for a significant period of time and readily replaceable if it does have to be replaced before the syringe has to be replaced. For this reason among others, a protective device for the repeatedly re-useable type of syringe requires various construction features not needed by protective devices for the one-time use disposable type of syringe.

Examples of prior art types of protective devices for syringes includes those shown and described in the following United States patents.

U.S. Pat. No. 4,752,290 discloses a needle bearing medical device of the disposable type having a tubular shield which can be held in three positions, one of which is a releasable needle covering position, the second of which is a releasable needle exposing position and the third is a non-releasable needle covering position from which the shield cannot be retracted for re-use.

U.S. Pat. No. 4,738,663 discloses a hypodermic needle shield which comprises a sleeve guide that is mounted on the syringe and secured to its flange, and a shield which travels on the sleeve guide between an extended and retracted position. When in the extended position wherein the shield covers the needle, the shield is locked in place where it can neither be retracted nor pulled off of the syringe but remains in place to cover the needle when the syringe with needle still attached is discarded.

U.S. Pat. No. 4,737,144 discloses a syringe having a protective sleeve that can be pushed forward to cover the needle after it has been used, the sleeve locking in place in the extended position from which it cannot be retracted.

U.S. Pat. No. 4,723,943 discloses a syringe having a sheath with an elongated slot to receive a guide lug on the barrel of the syringe. The rearwardly extending end of the slot in the sheath opens to a recess having a pair of laterally extending pockets or slots, one of which has a snap lock lip and the other has a shape and dimension to receive the lug snugly therein when the sleeve is rotated but from which the lug can be unseated for sliding the sheath back to its retracted position. When the sheath is in the extended position and rotated the opposite way for the lug to seat in the other pocket having the snap lock lip, the sheath cannot be rotated back to get the lug out of that pocket. The sheath is then locked permanently in place and the entire assembly is then discarded.

U.S. Pat. No. 4,702,739 discloses a syringe having a retractable sleeve covering the needle which retracts when the syringe is placed against the body of a patient, or self administrator, and the syringe pushed forward to insert the needle for injection of the medication. It is designed especially for those who have to administer injections to themselves, such as diabetics, and to reduce the fear or anxiety sometimes associated with seeing a needle about to be inserted through a person's skin.

U.S. Pat. No. 4,702,738 discloses a disposable syringe and sheath in which the sheath may be permanently locked in its extended position covering the needle for disposal of the entire unit after being used.

U.S. Pat. No. 4,693,708 discloses a syringe of the disposable type in which the needle is permanently attached and sealed within a tubular enclosure device to protect it from contamination until ready for use, at which time the end tab is torn away to open the forward end wall for the needle to project through when the tubular device is retracted to enable insertion of the needle into a patient. After use, the tubular device is pushed forwardly to cover the used needle and the unit then discarded.

U.S. Pat. No. 4,681,567 discloses a syringe having a slidable sheath to cover the needle and lock permanently in place after the needle has been used.

U.S. Pat. No. 4,631,057 discloses a syringe and sheath in which the forward end of the syringe barrel has a collar with an annular groove to receive a corresponding annular bead of the sheath when in the retracted position, and a one-way annular groove to receive a one-way annular snap lock projection of the sheath to lock it permanently in place when pushed to the extended position.

U.S. Pat. No. 4,425,120 discloses a syringe and sheath in which the barrel of the sheath has a pair of lugs, and the sheath has a pair of L-shaped slots to receive respective ones of the lugs whereby the sheath can be locked in both the retracted and extended positions by rotating to seat the respective lugs in the laterally extending leg of the respective slot.

The protective sheath in accordance with the present invention slides on the barrel of the repeatedly re-useable syringe between a retracted position, in which the screw threads of the needle connecting projection are exposed for connecting a hypodermic needle thereto, and an extended position after the needle has been used to cover the needle until it can be disposed of. Since the syringe in this case is of the re-useable kind, the used needle has to be disconnected from the syringe. The protective sheath therefore is provided with apertures which overlie the hub of the needle assembly when the sheath is in its extended position covering the needle, whereby the user can reach through such apertures to unscrew the hub of the needle assembly from the threads of the needle connecting projection. The needle assembly then drops to the bottom of the extended sheath which the user holds in a horizontal position to prevent the uncoupled needle assembly from dropping out. The unit is then carried to a disposal container whereupon the syringe and its extended sheath can be tipped downward to let the used needle drop through the open forward end wall of the sheath into the container for disposal.

The sheath and syringe barrel include cooperating stop members to prevent removal of the sheath from the forward or needle connecting end of the syringe. The sheat is removable from the syringe barrel for cleaning, sterilization and the like, by unscrewing the syringe barrel from the plunger mechanism and sliding the sheath off from the reward, or plunger connecting end of the barrel. The sheath is replaced on the barrel from the same rearward end, and the barrel then screwed in place in the receiving recess of the plunger assembly.

Some of the permanent re-useable syringes are of the type in which the barrel cavity is bounded by an imperforate wall, and the cartridge of injectable material is placed in the barrel of the syringe from its rearward end while uncoupled from the plunger assembly.

Other types of permanent, re-useable syringes have an elongated slot in the wall of the barrel wide enough and long enough to place a cartridge having the injectable substance in the barrel through such opening or slot in its side wall.

The protective sheath in accordance with the present invention may be used with both types of permanent, re-useable syringes. When used with the type in which the cartridge is placed in the syringe barrel through the opening in its side wall, the sheath is pushed forward to its extended position which exposes the elongated slot or opening to insert the cartridge. The sheath is then moved back to its retracted position which exposes the threads of the needle connecting projection at the forward end of the syringe barrel. When the needle assembly is connected, the syringe is ready for use. After use on a patient, the sheath is moved to its extended position where it completely covers the used needle. The needle assembly is then disconnected as described above while the protective sheath is still in its extended position and the disconnected needle then carried in the sheath held in the horizontal position to the disposal container for disposal of the used needle assembly.

Hypodermic needles come in a two-part sealed cartridge, having a closed cylindrical chamber in which the needle extends with the hub frictionally held by the cylindrical wall bounding the opening and a removable cap which covers the hub until the user is ready to use the needle. When the cap is removed, the internal threads of the hub of the needle assembly are exposed for screwing on to the threaded needle connecting projection at the forward end of the syringe barrel while the needle itself is still within the chamber of the cartridge it comes in. After the needle assembly has been screwed on to the syringe, the cartridge chamber is pulled away to expose the needle. At this time, the sheath of the present invention may be pushed forward to its extended position wherein it completely covers the needle. The syringe with sterile needle attached may then be laid down temporarily without the needle touching a non-sterile surface.

In the prior art practice when it became necessary to temporarily lay the syringe down after a sterile needle had been connected and its original cartridge chamber removed, the users would put the original cartridge chamber back on the needle assembly to protect it from touching a non-sterile surface. This often results in needle sticks while the user tries to insert the needle back into the relatively small diameter chamber of the original needle cartridge. The Center for Disease Control has now recommended that syringe needles not be re-capped after the original cartridge chamber has been removed in order to prevents doctors, dentists and other health care providers from accidentally receiving a needle stick while trying to re-cap the needle.

The protective sheath in accordance with this invention makes it unnecessary to have other devices in the treatment area for the protection of uncapped needles connected to a syringe.

To give the sheath greater stability and to help hold it in axial alignment with the syringe barrel while in the extended position, especially when laid down on a table or the like where forces may be applied against the forward end of the extended sheath tending to move it out of axial alignment whereby its peripheral wall could come in contact with the sterile needle, a plurality of longitudinal ribs are provided on the syringe barrel to seat in a corresponding plurality of longitudinal grooves formed in the wall of the sheath opening to its inner surface. The cross-sectional dimension and configuration of the sheath corresponds closely to that of the syringe barrel for a snug fit but which permits the sheath to readily slide on the barrel between its retracted and extended positions. The longitudinal ribs and grooves enhance and re-inforce the stability of the sheath in axial alignment with the syringe barrel. The sheath has a longitudinal dimension long enough to extend beyond the needle connected to the syringe and with a sufficiently long portion of sheath still on the barrel of the syringe, with the ribs of the syringe barrel seated in the grooves of the sheath, to hold the sheath in axial alignment with the syringe barrel when the sheath is in its extended position Stop means are provided as set forth in detail in the description of the preferred embodiment to prevent the sheath from moving forward on the syringe barrel beyond its intended point. A releasable lock member is also provided to lock the sheath in its extended position, but releasable to enable moving the sheath back to its retracted position. The lock member is also described in detail later herein.

The sheath is preferably made of a durable long lasting material which is also heat resistant and pressure resistant, such as autoclavable acrylic or a metal such as stainless steel. The sheath is preferably transparent, but it need not be.

While the protective sheath in accordance with this invention is shown and described herein for use with one kind of syringe, it is useable with various other types of syringes which have an elongated barrel, a plunger or other operating mechanism at one end and a hypodermic needle connected at the other end.

SUMMARY OF THE INVENTION

It is an object of the invention to provide a re-useable protective sheath for re-useable syringes to protect against accidental needle sticks.

It is an object of the invention to provide a re-useable protective sheath for re-useable syringes having means to enable disconnection of a used needle from the syringe while the sheath is in its extended position covering the needle.

It is an object of the invention to provide a re-useable protective sheath for re-useable syringes in which the sheath and syringe have a plurality of longitudinal ribs seated in corresponding longitudinal grooves to enhance and re-inforce the ability of the sheath to stay in axial alignment with the barrel of the syringe when in its extended position covering the needle connected to the syringe.

It is an object of the invention to provide a re-useable protective sheath for re-useable syringes in which stop means are provided to prevent moving the sheath forward on the syringe barrel beyond its intended point, wherein a sufficient portion of the sheath remains on the barrel to hold it in axial alignment with the barrel when in its extended position.

It is an object of the invention to provide a reuseable protective sheath for re-useable syringes having releasable lock means, to lock the sheath in its extended position covering the needle connected to the syringe and to release the sheath for movement back to its retracted position for re-use with the re-useable syringe.

DESCRIPTION OF PREFERRED EMBODIMENT

Figure 1:
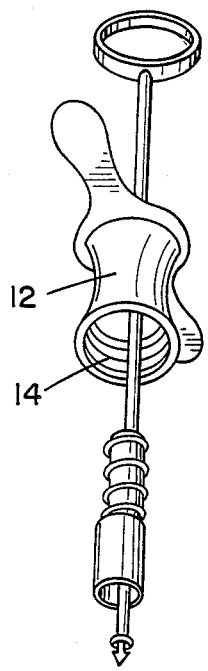
FIG. 1 is a perspective view of a plunger assembly of a re-useable syringe.
Figure 3:
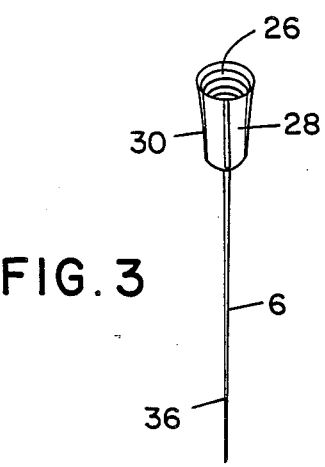
FIG. 3 is a hypodermic needle assembly for connection to the re-useable syringe barrel shown in FIG. 2.
Figure 2:
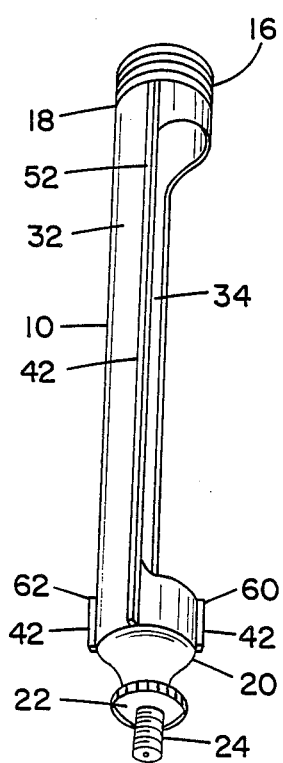
FIG. 2 is a perspective view of a barrel of a re-useable syringe for connection to the plunger assembly of FIG. 1.
Figure 4:
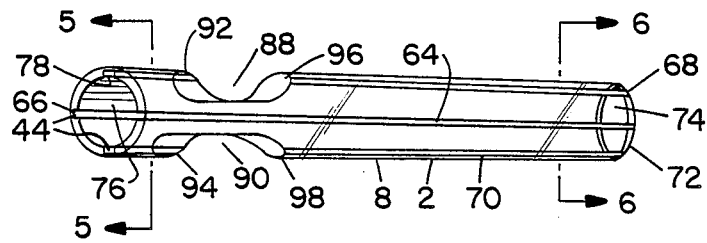
FIG. 4 is a perspective view of a protective shield or tubular sheath for mounting on the barrel of the re-useable syringe and for reciprocal movement thereon.
Figure 5:
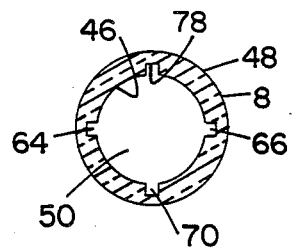
FIG. 5 is a section view of the tubular sheath taken on line 5—5 of FIG. 4.
Figure 6:
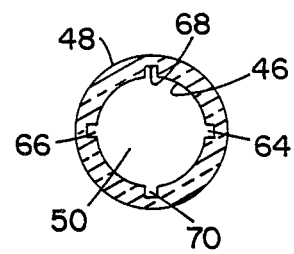
FIG. 6 is a section view of the tubular sheath taken on line 6—6 of FIG. 4.
Figure 7:
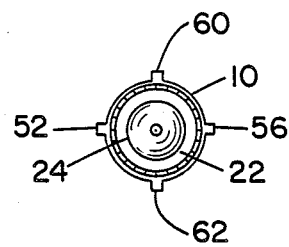
FIG. 7 is an end view from the front of the syringe barrel shown in FIG. 2.
Figure 8:
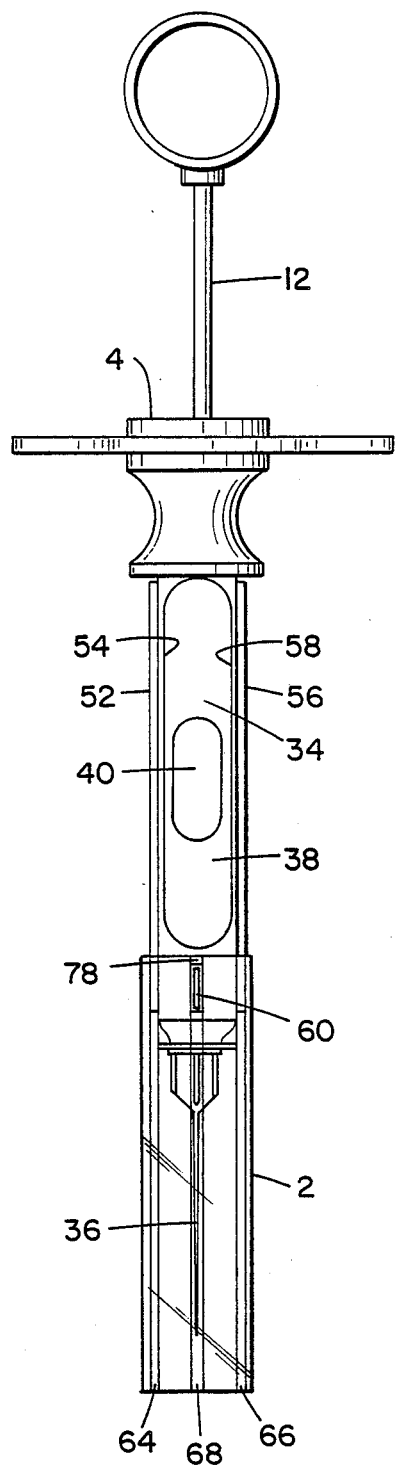
FIG. 8 is an elevation view of a re-useable syringe with plunger assembly, barrel and needle assembly connected and with the protective tubular sheath in its extended position to cover the hypodermic needle, showing the elongated slot for placing a cartridge in the barrel cavity in plan view and with the shorter slot on the opposite side of the barrel also visible.
Figure 9:
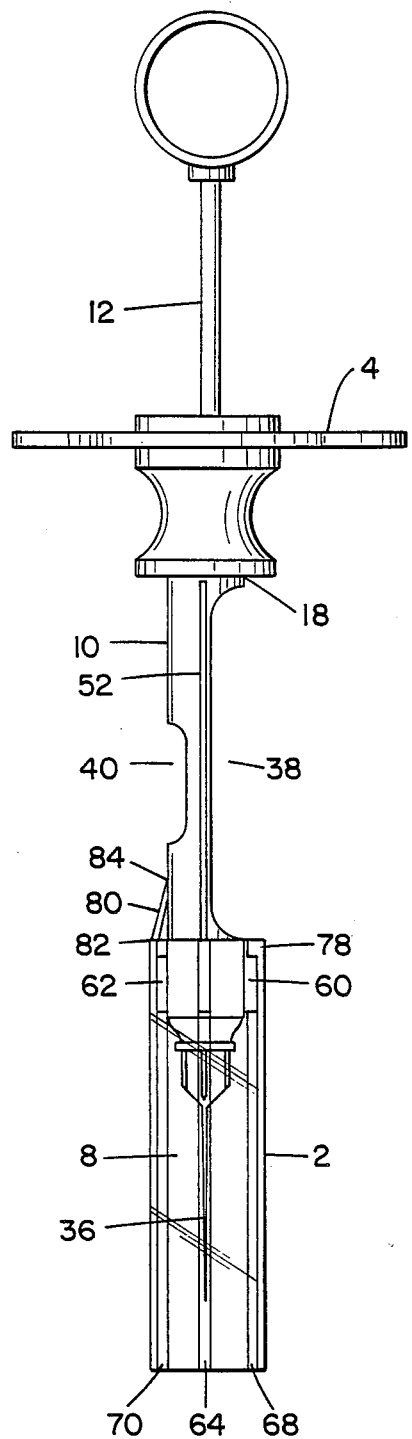
FIG. 9 is an elevation view as in FIG. 8 but with the syringe barrel rotated ninety degrees with the elongated slots opening to the barrel cavity shown in side elevation.
Figure 10:
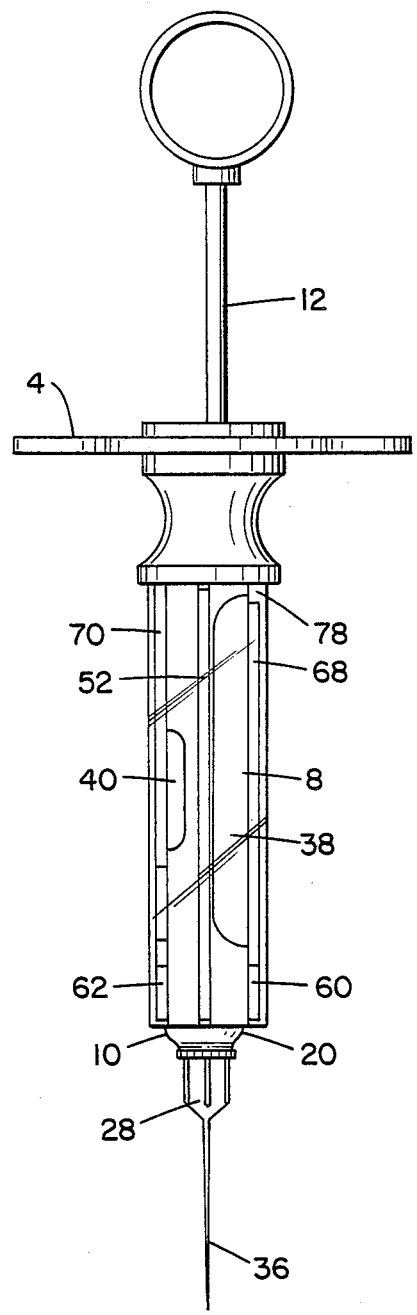
FIG. 10 is an elevation view of the syringe shown in FIG. 9 but with the protective tubular sheath shown in its retracted position.

A protective shield 2 for syringes 4 in accordance with the present invention to protect users from unintended contact with attached needles 6 comprises a preferably transparent tubular sheath 8 mounted on the barrel 10 of the anesthetic syringe 4 used in the medical and dental professions, the tubular sheath 8 being mounted for sliding reciprocal movement between a retracted position wherein the attached needle 6 is exposed and an extended position wherein the attached needle 6 is bounded by and enclosed within the transparent tubular sheath 8.

The syringes for which this invention is particularly adapted are those which are made and designed for re-use, and which are usually made of a metal such as stainless steel. For such syringes, the tubular sheath 8 has to be reciprocally movable in both directions while mounted on the syringe, both from the retracted to the extended position and in the opposite direction from the extended to the retracted position. The tubular sheath 8 in accordance with the present invention is itself re-useable as long as the syringe itself is reusable, although the sheath can be removed and replaced if and when necessary. The sheath 8 is made of a durable and preferably transparent material such as an acrylic or similar synthetic plastic material. It may also be made of metal, such as stainless steel.

The barrel 10 of the re-useable syringe 4 is removable from the plunger operating mechanism 12. The plunger operating mechanism 12 includes an internally threaded plunger coupling recess 14 to receive the corresponding barrel 10 at its plunger coupling end 18. The barrel 10 terminates at its opposite end 20 in a needle coupling assembly 22 comprising a reduced diameter externally threaded needle coupling projection 24 to be received in the corresponding internally threaded needle coupling recess 26 in the hub 28 of one-time-use needle assemblies, such as needle assembly 30, which are screwed on to the re-useable syringe 4 for one time use on one patient. The needle assembly 30 is then unscrewed from the syringe 4 and discarded.

The barrel 10 is elongated and has an arcuate peripheral wall 32 bounding a cylindrical barrel cavity 34 to receive cartridges of anesthetic material or the like (not shown) for injection into a patient through the needle 36 of the needle assembly 30 by operation of the plunger operating mechanism 12.

Some of the barrels used on re-useable syringes 4 have a completely solid arcuate peripheral wall and the cartridges of anesthetic material are inserted into the cylindrical cavity by unscrewing the externally threaded plunger coupling projection 16 of the barrel from the internally threaded coupling recess 14 of the plunger operating mechanism 12 and inserting the cartridge through the open end 36 of the barrel 10. The barrel is then re-coupled to the plunger operating mechanism, with the cartridge positioned for engagement by the plunger to expel its contents out through the needle 36.

Other barrels used on re-useable syringes 4 have an elongated slot 38 or cut-away opening of approximately semi-circular cross-section opening to the cylindrical barrel cavity 34 in which the width or cross-sectional dimension of slot 38 is substantially equal to the diameter of cylindrical barrel cavity 34. The longitudinal dimension of the elongated slot 38 corresponds to that of a cartridge of anesthetic material to be received in the cylindrical barrel cavity 34, whereby such cartridge can be placed in the cylindrical barrel cavity 34 through the elongated slot 38.

A second elongated slot 40 of shorther longitudinal dimension and narrower cross-section than slot 38 is provided in the arcuate peripheral wall 32 opening to the cylindrical barrel cavity 34 at a location diametrically opposite from slot 38. The slot 40 has a cross-section wide enough for a user to insert this finger tip therein far enough to push a cartridge out of the cavity 34 far enough to be grasped by the user's other hand for removal.

In accordance with the present invention, the syringe barrel 10 may have one or more longitudinally extending ribs 42 to be received in corresponding longitudinally extending grooves 44 formed on the inner surface 46 of the cylindrical peripheral wall 48 of the tubular sheath 8 and opening to the cylindrical sheath cavity 50.

One longitudinal extending rib 52 may be positioned along and parallel to one side edge 54 of elongated slot 38 and a second longitudinally extending rib 56 may be positioned along and parallel to the opposite side edge 58 of elongated slot 38. The ribs 52 and 56 extend the length, or longitudinal dimension, of the barrel 10, one end thereof termination at the externally threaded plunger coupling projection 16 of the barrel 10 and the opposite end thereof terminating at the needle coupling projection 24 of the barrel 10.

A third longitudinally extending rib 60 which is relatively short extends inwardly of the barrel 10 from its end adjacent the reduced diameter needle coupling projection 24, radially displaced ninety degrees from longitudinal ribs 52 and 56 and in line with the mid-line of elongated slot 38, and terminates at the junction with slot 38. Slot 38 terminates about a quarter inch to a half inch short of the end of barrel 10 adjacent needle coupling projection 24, so rib 60 is about a quarter inch to a half inch long.

A fourth longitudinal rib 62 which is also relatively short is located diametrically opposite from the third longitudinal rib 60 on the barrel 10, and extends inwardly thereof from its end adjacent the reduced diameter needle coupling projection 24 a short distance corresponding to that of the longitudinal dimension of longitudinal rib 60. Thus rib 62 is also about a quarter inch to a half inch in length.

The tubular sheath 8 for use on the barrel 10 having longitudinal ribs 52, 56, 60 and 62 is provided with corresponding longitudinal grooves 64, 66, 68 and 70 formed on the inner surface 46 of cylindrical peripheral wall 48 of the tubular sheath 8 and opening to the cylindrical sheath cavity 50, each radially displaced ninety degrees from adjacent ones of said grooves. The longitudinal grooves 64, 66, 68 and 70 extend the length of the sheath 8 and each groove opens to the forward end 72 of the sheath 8 which has an open forward end wall 74 and an open rearward end wall 76.

The tubular sheath 8 is mounted on the syringe barrel 10 by first unscrewing the barrel 10 from the coupling recess 14 of the plunger operating mecchanism 12, and positioning the open end wall 74 of the sheath 8 in line with the plunger coupling end 18 of the syringe barrel 10, with open ends of diametrically opposite grooves 64 and 66 in line to receive corresponding diametrically opposite ribs 52 and 56 of the barrel 10 respectively. The sheat 8 is then slid forward on the barrel 10 until the open rearward end wall 76 of the sheath 8 passes the externally threaded plunger coupling projection 16 of the barrel 10 and is immediately adjacent thereto. At such time the open forward end wall 74 of the sheath 8 is immediately adjacent the forward end of the arcuate peripheral wall 32 of the barrel 10 and its junction with the forwardly projecting reduced diameter needle coupling projection 24. The length or longitudinal dimension of the tubular sheath 8 corresponds to that of the arcuate peripheral wall 32 of the syringe barrel 10 between the threaded plunger coupling projection 16 at one end and the threaded needle coupling projection 24 at the opposite end.

When the sheath 8 is pushed on to the syringe barrel 10 far enough to reach the two diametrically opposite short longitudinal ribs 60 and 62, the open ends of diametrically opposite grooves 68 and 70 are in line to receive corresponding ones of the ribs 60 and 62 respectively. Groove 68 which receives rib 60 has a stop element 78 at its end adjacent the reward end wall 76 of sheath 8. Thus, when the sheath 8 is pushed further forward on the syringe barrel 10 so its forward open end wall 74 projects forwardly beyond the forward end of the syringe barrel 10, the stop element 78 in groove 68 at its rearward end will abut against the rearward end of the short longitudinal rib 60 to prevent any further forward movement of the sheath 8 on the syringe barrel 10. At such time, the tubular sheath 8 extends forwardly of the syringe barrel 10 far enough to cover and surround a needle 36 of a needle assembly 30 coupled to the needle coupling projection 24 at the forward end of the syringe barrel 10.

A detent member in the form of a metal spring 80 is provided on the peripheral wall 32 of the syringe barrel 10, in line with and inwardly or rearwardly from the short longitudinal rib 62, and positioned whereby the forwardly extending and movable end 82 of spring 80 clears the rearward end wall 76 of the sheath 8 when stop element 78 in groove 68 abuts against the rearward end of rib 60 to prevent further forward movement of sheath 8 on syringe barrel 10. The movable end 82 of spring 80 is normally biased outwardly from the surface of the syringe barrel 10, and the non-movable opposite end 84 of the spring 80 is welded, riveted or otherwise secured to the surface of the barrel 10 at a point rearwardly of the outwardly biased movable end 82. Thus, the spring 80 extends at a diagonal diverging outwardly from the surface of the barrel 10 in the direction from its non-movable end 84 to its movable end 82 and in the direction of forward movement of the sheath 8 on the syringe barrel 10. Thus, when the sheath 8 is being mounted on the barrel 10, the forward end 72 of the sheath passes over the connected non-movable end 84 of the spring 80 and presses the diagonally extending movable end 82 downward against the surface of the syringe barrel 10 as the tubular sheath 8 continues forward on the barrel 10.

When the sheath 8 has been pushed forwardly to the point that stop element 78 abutting against rib 60 prevents further forward movement of the sheath 8 on the barrel 10 and the movable end 82 of the spring 80 clears the reward end wall 76 of the sheath 8, the outwardly biased movable end 82 of the spring 80 springs outwardly a sufficient distance to face the annular edge 86 of the rearward end wall 76 of sheath 8 to thereby prevent the sheath 8 from being moved in the opposite rearward direction on the syringe barrel 10 until the movable end 82 of spring 80 is depressed against the surface of the syringe barrel 10. The movable end 82 of spring 80 then clears the annular edge 86 of rearward end wall 76 permitting the sheath to slide rearward on the syringe barrel 10.

When stop element 78 abuts against rib 60 and the movable end 82 of spring 80 is in line to abut against the annular edge 86 of rearward end wall 76, the tubular sheath 8 is locked in place in its extended position wherein the needle 36 of an attached needle assembly 30 is bounded by and enclosed within the tubular sheath 8.

A pair of elongated access apertures 88 and 90 are provided in the cylindrical peripheral wall 48 of the tubular sheath 8, located in diametrically opposite positions thereon, aperture 88 being axially aligned with groove 68 and asperture 90 being axially aligned with groove 70, and each aperture 88 and 90 being positioned inward of the cylindrical peripheral wall 48 of sheath 8 and forwardly from the rearward end wall 76 thereof a sufficient distance for apertures 88 and 90 to overlay the hub 28 of needle assembly 30 when the sheath 8 is locked in placed in its extended position with stop element 78 in groove 68 abutting against rib 60 on the syringe barrel 10. Such distance of apertures 88 and 90 inward of sheath 8 and forward from its rearward end wall 76 positions the rearward edges 92 and 94 of such apertures about one-quarter inch to about one-half inch from the rearward end wall 76, and the forward edges 96 and 98 thereof about an inch to an inch and a half therefrom. The longitudinal dimension of apertures 88 and 90 may therefore be about three-quarters of an inch to an inch. Their lateral dimension may be about a quarter-inch to a half-inch. The longitudinal and lateral dimension of access apertures 88 and 90 is any convenient size that enables a user to insert his thumb through one of such apertures and a finger through the other far enough to reach the hub 28 of needle assembly 30 in place on the needle coupling projection 24 of syringe barrel 10, and to rotate it in the direction that will unscrew the hub 28 from the needle coupling projection 24 of the syringe 4 while the tubular sheath 8 is locked in its extended position that protects the user from accidental contact with the needle 36.

When the needle assembly 30 is uncoupled from the syringe barrel 10 after its one time use with a single patient the syringe 4 is held in the horizontal position whereupon the needle assembly 30 and its used needle 36 drop to the inner surface 46 of the cylindrical wall 48 of tubular sheath 8. The uncoupled needle assembly 30 and needle 36 may then be carried while holding the syringe 4 in the horizontal position to a disposal container. The needle assembly 30 and used needle 36 then fall through the open forward end wall 74 of the sheath 8 and into the disposal container when the syringe 4 is tipped downwardly to enable the needle assembly 30 and needle 36 to slide out.

This construction makes it possible for the dentist, physian and other health care workers to remove and dispose of contaminated used hypodermic needles from re-usable syringes without any risk of coming in contact with the sharp end of the needle and in fact without coming in contact with any part of the needle itself which had been inserted into a patient and on which contaminated blood, or other fluids, or bacteria may have become attached. The only part of the needle assembly that a user can even have access to when the protective sheath in accordance with this invention is locked in place in its extended position is the hub portion, which as the most rearward part of the needle assembly is least likely to have any contaminated substance thereon and in any event cannot itself puncture the skin of a user.

After cleaning and sterilizing, the tubular sheath 8 may then be moved back from its extended position to its retracted position by depressing the movable end 82 of the metal spring 80 against the surface of the syringe barrel 10 whereby it clears the annular edge 86 of rearward end wall 76 of the sheath 8, thereby enabling the user to slide the tubular sheath rearward to its fully retracted position. At such time, the forward end wall 74 of the tubular sheath 8 lies rearwardly of the externally threaded needle coupling projection 24 of the syringe 4, thereby making it accessible for screwing the hub of a new needle assembly and its needle thereon.

New and uncontaminated needle assemblies come in a two-part protective tubular case, having a cover which when removed exposes the hub portion of the needle assembly to enable screwing the hub on to the threaded needle coupling projection of the syringe. After the hub has been securely threaded on to the syringe, the other part of the two-part protective tubular case is then pulled forward and away from the needle assembly thereby exposing the needle for use. After it has been used, the protective sheath in accordance with this invention is pushed forward to its extended position and locked in place as described above which covers the needle assembly and its used needle thereby fully protecting the users while the needle assembly is disconnected from the syringe and carried to a disposal container for disposal. Thus, this invention enables the user to have protection from the time of initial connection of the needle to the syringe until disposal after use, where permanent types of syringes are concerned which are used over and over again with new needle assemblies connected and disconnected for each use.

I claim:

1. A protective device for a syringe of the type having an elongated barrel to receive a cartridge therein containing a substance to be injected into a patient by operation of said syringe, having a plunger assembly connected to said barrel at one end to operate said syringe and having needle connecting means to connect a hypodermic needle to said syringe at the other end thereof, wherein said protective device comprises a sheath having a peripheral wall bounding a through channel opening at one end to an open rearward end wall and at the opposite end to an open forward end wall, said through channel having a cross-sectional dimension and configuration corresponding to that of said elongated of said syringe to receive it therein and to enable sliding said sheath forwardly on said barrel in the direction toward said needle connecting means and rearwardly thereon in the direcction toward said plunger assembly, said peripheral wall of said sheath having an elongated needle protective portion, said sheath being reciprocally movable on said barrel of said syringe between a retracted position wherein said needle protective portion of said peripheral wall of said sheath is positioned to enable access to said needle connecting means of said syringe and an extended needle protecting position wherein said needle protective portion of said peripheral wall of said sheath extends forwardly of said barrel of said syringe, said elongated needle protective portion of said peripheral wall of said sheath which extends forwardly of said barrel of said syringe having a longitudinal dimension at least as great as that of a said hypodermic needle when connected to said needle connecting means of said syringe, said protective device including needle disconnect means to enable disconnecting said hypodermic needle from said syringe while said sheath is in its said extended needle protecting position.

2. A protective device for a syringe of the type having an elongated barrel to receive a cartridge therein containing a substance to be injected into a patient by operation of said syringe, having a plunger assembly connected to said barrel at one end to operate said syringe and having needle connecting means to connect a hypodermic needle to said syringe at the other end thereof, wherein said protective device comprises a sheath having a peripheral wall bounding a through channel opening at one end to an open rearward end wall and at the opposite end to an open forward end wall, said through channel having a cross-sectional dimension and configuration corresponding to that of said elongated barrel of said syringe to receive it therein and to enable sliding said sheath forwardly on said barrel in the direction toward said needle connecting means and rearwardly thereon in the direction toward said plunger assembly, said peripheral wall of said sheath having an elongated needle protective portion, said sheath being reciprocally movable on said barrel of said syringe between a retracted position wherein said needle protective portion of said peripheral wall of said sheath is positioned to enable access to said needle connecting means of said syringe and an extended needle protecting position wherein said needle protective portion of said peripheral wall of said sheath extends forwardly of said barrel of said syringe, said elongated needle protective portion of said peripheral wall of said sheath which extends forwardly of said barrel of said syringe having a longitudinal dimension at least as great as that of a said hypodermic needle when connected to said needle connecting means of said syringe, said protective device including lock means to lock said sheath in said extended needle protective position, said lock means being operable between a locking position to lock said sheath in said extended needle protecting position and an unlocking position to release said sheath for moving from said extended needle protecting position to said retracted needle connecting position.

3. A protective device for a syringe of the type having an elongated barrel to receive a cartridge therein containing a substance to be injected into a patient by operation of said syringe, having a plunger assembly connected to said barrel at one end to operate said syringe and having needle connecting means to connect a hypodermic needle to said syringe at the other end thereof, wherein said protective device comprises a sheath having a peripheral wall bounding a through channel opening at one end to an open rearward end wall and at the opposite end to an open forward end wall, said through channel having a cross-sectional dimension and configuration corresponding to that of said elongated barrel of said syringe to receive it therein and to enable sliding said sheath forwardly on said barrel in the direction toward said needle connecting means and rearwardly thereon in the direction toward said plunger assembly, said peripheral wall of said sheath having an elongated needle protective portion, said sheath being reciprocally movable on said barrel of said syringe between a retracted position wherein said needle protective portion of said peripheral wall of said sheath is positioned to enable access to said needle connecting means of said syringe and an extended needle protecting position wherein said needle protective portion of said peripheral wall of said sheath extends forwardly of said barrel of said syringe, said elongated needle protective portion of said peripheral wall of said sheath which extends forwardly of said barrel of said syringe having a longitudinal dimension at least as great as that of a said hypodermic needle when connected to said needle connecting means of said syringe, said protective device including stop means to stop forward sliding movement of said sheath before the said rearward end wall thereof passes beyond the end of said barrel having said needle connecting means thereat.

4. A protective device for a syringe as set forth in claim 1, wherein said needle disconnect means includes at least one access aperture in said peripheral wall of said sheath positioned thereon to provide access to said needle connecting means while said sheath is in its said extended needle protecting position.

5. A protective device for a syringe as set forth in claim 2, wherein said lock means includes a lock member having an abutment surface positioned on said barrel of said syringe rearward of said open rearward end wall of said sheath when it is in its said extended needle protecting position, said peripheral wall of said sheath having a rear peripheral edge surrounding said open rearward end wall thereof, said abutment surface of said lock member being movable between an abutting position wherein it abuts against said rear peripheral edge to prevent rearward movement of said sheath on said barrel of said syringe and a release position wherein said sheath is released for rearward movement on said barrel of said syringe, said abutment surface of said lock member being normally biased toward its said abutting position.

6. A protective device for a syringe as set forth in claim 5, wherein said lock member comprises an elongated spring member having a stationary connecting end for connection to said barrel of said syringe and a movable end having said abutment surface thereon, said movable end of said spring member being normally biased outwardly from said barrel of said syringe to said abutting position and movable inwardly toward and against said barrel of said syringe to said release position, said spring member extending at a diagonal from said barrel of said syringe when said movable end thereof is in its normally biased outwardly position and diverging therefrom as it extends in the direction toward said end of said barrel having said needle connecting means thereat.

7. A protective device for a syringe as set forth in claim 3, wherein said stop means includes a longitudinal groove in said peripheral wall of said sheath opening to said through channel thereof, an abutment surface in said longitudinal groove at the end of said sheath adjacent said rearward end wall thereof, a rib for positioning on said barrel of said syringe toward said end thereof having said needle connecting means thereat to be received in said longitudinal groove and to slide therein as said sheath is moved from said retracted position to said extended position, said rib being positioned to abut against said abutment surface in said groove and to prevent further forward movement of said sheath on said barrel of said syringe when said sheath has reached its said extended needle protecting position.

8. A protective device for a syringe as set forth in claim 1, including at least one longitudinal rib for positioning on said barrel of said syringe to extend from said end thereof having said plunger assembly connected thereto to said end thereof having said needle connecting means thereat, said peripheral wall of said sheath having a corresponding longitudinal groove opening to said through channel to receive said longitudinal rib therein when said sheath is mounted on said barrel of said syringe, said longitudinal groove in said peripheral wall of said sheath extending from the end thereof adjacent said open rearward end wall to the end thereof adjacent said open forward end wall, said longitudinal rib being slidable in said longitudinal groove as said sheath is moved on said barrel of said syringe between its said retracted and extended positions.

9. A protective device and syringe, wherein said syringe includes an elongated barrel to receive a cartridge therein containing an injectable substance to be injected into a patient by operation of said syringe, a plunger assembly removably connected to said barrel at a first barrel end thereof to operate said syringe, needle connecting means to connect a hypodermic needle to said syringe at the opposite second barrel end of said barrel, said protective device comprising a sheath having a peripheral wall bounding a through channel opening at a first sheath end to an open rearward end wall and at the opposite second sheath end to an open forward end wall, said through channel having a cross-sectional dimension and configuration to receive said elongated barrel of said syringe therein and to enable sliding said sheath rearwardly on said barrel in the direction toward said first barrel end and forwardly thereon toward said second barrel end, said peripheral wall of said sheath having an elongated needle protective portion, said sheath being reciprocally movable on said barrel of said syringe between a retracted needle connecting position wherein said needle protective portion of said peripheral wall of said sheath is positioned to enable access to said needle connecting means of said syringe and an extended needle protecting position wherein said needle protective portion of said peripheral wall of said sheath extends forwardly of said barrel of said syringe, said elongated needle protective portion of said peripheral wall of said sheath which extends forwardly of said barrel of said syringe having a longitudinal dimension at least as great as that of a said hypodermic needle when connected to said needle connecting means of said syringe, said syringe being made of a durable materials for repeated re-use of said syringe, said barrel of said syringe and said plunger assembly being removable one from the other for thorough cleaning and re-connectible for repeated re-use of said syringe.

10. A protective device and syringe as set forth in claim 9, wherein said protective device includes needle disconnect means to enable disconnecting said hypodermic needle from said syringe while said sheath is in its said extended needle protecting position.

11. A protective device and syringe as set forth in claim 10, wherein said needle diconnect means includes at least one access aperture in said peripheral wall of said sheath positioned thereon to provide access to said needle connecting means for disconnecting a hypodermic needle from said syringe while said sheath is in its said extended needle protecting position.

12. A protective device and syringe as set forth in claim 9, including lock means to lock said sheath in said extended needle protecting position, said lock means being operable between a locking position to lock said sheath in said extended needle protecting position and an unlocking position to release said sheath for moving from said extended needle protecting position to said retracted needle connecting position.

13. A protective device and syringe as set forth in claim 12, wherein said lock means includes a lock member having an abutment surface positioned on said barrel of said syringe rearward of said first sheath end when said sheath is in its said extended needle protecting position, said peripheral wall of said sheath having a rear peripheral edge surrounding said open rearward end wall thereof at said first sheath end, said abutment surface of said lock member being movable between an abutting position sherein it abuts against said rear peripheral edge to prevent rearward movement of said sheath on said barrel of said syringe and a release position wherein said sheath is released for rearward movement on said barrel of said syringe.

14. A protective device and syringe as set forth in claim 13, wherein said lock member comprises as elongated spring member having a stationary end affixed to said barrel of said syringe and a movable end having said abutment surface thereon, said movable end of said spring member being normally biased outwardly from said barrel of said syringe to said abutting position and movable inwardly toward and against said barrel of said syringe to said release position, said spring member extending at a diagonal from said barrel of said syringe when said movable end thereof is in its normally biased outwardly position and diverging therefrom as it extends in the direction toward said second barrel end.

15. A protective device and syringe as set forth in claim 9, including stop means to stop forward sliding movement of said sheath before the said first sheath end having said open rearward end wall thereof passes beyond the said second barrel end having said needle connecting means thereat.

16. A protective device and syringe as set forth in claim 15, wherein said stop means includes a longitudinal groove in said peripheral wall of said sheath opening to said through channel thereof, an abutment surface in said longitudinal groove at the said first sheath end adjacent said open rearward end wall thereof, a rib positioned on said barrel of said syringe toward said second barrel end having said needle connecting means thereat to be received in said longitudinal groove and to slide therein as said sheath is moved from said retracted position to said extended position, said rib being positioned to abut against said abutment surface in said groove and to prevent further forward movement of said sheath on said barrel of said syringe when said sheath has reached its extended needle protecting position.

17. A protective device and syringe as set forth in claim 9, wherein said peripheral wall of said barrel of said syringe is cylindrical, a first elongated slot in said peripheral wall of said barrel having a longitudinal and lateral dimension to receive a said cartridge having a said injectable substance through said first elongated slot to seat in said barrel in position for operable contact by said plunger assembly, a first elongated rib on said barrel extending parallel to and near one side of said first elongated slot, a second longitudinal rib on said barrel extending parallel to and near the opposite side of said first elongated slot, a first longitudinal groove in said peripheral wall of said sheath opening to said through channel thereof, a second longitudinal groove in said peripheral wall of said sheath opening to said through channel thereof, said first and second longitudinal grooves being positioned to receive respective ones of said first and second longitudinal ribs therein when said sheath is mounted on said barrel for sliding engagement therewith as said sheath is moved between its said retracted and extended positions.

18. A protective device and syringe as set forth in claim 17, wherein the lateral dimension of said first elongated slot is substantially equal to the diameter of said through channel bounded by said cylindrical peripheral wall of said barrel, said first longitudinal rib extends adjacent to one side of said first elongated slot, said second longitudinal rib extends adjacent to the opposite side of said first elongated slot, said first and second longitudinal ribs being diametrically opposite from each other, a second elongated slot in said peripheral wall of said barrel opposite from said first elongated slot, said second elongated slot having a longitudinal and lateral dimension large enough for a user to extend an object therethrough to push a said cartridge outwardly of said barrel, a short third longitudinal rib on said barrel extending from said second barrel end toward said first elongated slot and axially aligned with the longitudinal axis of said first elongated slot, a short fourth longitudinal rib on said barrel extending from said second barrel end toward said second elongated slot and axially aligned with the longitudinal axis of said second elongated slot, a third longitudinal groove in said peripheral wall of said sheath opening to said through channel thereof, a fourth longitudinal groove in said peripheral wall of said sheath opening to said through channel thereof, said third and fourth longitudinal grooves being positioned to receive respective ones of said third and fourth longitudinal ribs therein when said sheath is mounted on said barrel for sliding engagement therewith as said sheath is moved between its said retracted and extended positions.

* * * * *

UNITED STATES PATENT AND TRADEMARK OFFICE
CERTIFICATE OF CORRECTION

PATENT NO. : 4,915,701

DATED : April 10, 1990

INVENTOR(S) : Douglas R. Halkyard

It is certified that error appears in the above-identified patent and that said Letters Patent is hereby corrected as shown below:

Column 2, line 20, delete "sheat" and insert - -sheath- -

Column 2, line 64, delete "sheat" and insert - -sheath- -

Column 2, line 67, delete "reward," and insert - -rearward,- -

Column 7, line 28, delete "mecchanism" and insert - -mechanism- -

Column 8, line 49, delete "asperture" and insert - -aperture- -

In The Claims

Column 10, Claim 1, line 17, after "elongated" insert - -barrel- -

Column 13, Claim 9, line 12, delete "materials" and insert
    - -material- -

UNITED STATES PATENT AND TRADEMARK OFFICE
CERTIFICATE OF CORRECTION

PATENT NO. : 4,915,701

DATED : April 10, 1990

INVENTOR(S) : Douglas R. Halkyard

It is certified that error appears in the above-identified patent and that said Letters Patent is hereby corrected as shown below:

Column 13, Claim 13, line 45, delete "sherein" and insert
- -wherein- -

Column 13, Claim 14, line 51, delete "as" and insert - -an- -.

Signed and Sealed this

Second Day of July, 1991

*Attest:*

HARRY F. MANBECK, JR.

*Attesting Officer*  *Commissioner of Patents and Trademarks*